United States Patent [19]

Harter

[11] Patent Number: 5,022,388

[45] Date of Patent: Jun. 11, 1991

[54] PATIENT TABLE APPARATUS

[75] Inventor: Robert T. Harter, Billings, Mo.

[73] Assignee: Health Care Manufacturing, Inc., Springfield, Mo.

[21] Appl. No.: 395,647

[22] Filed: Aug. 18, 1989

[51] Int. Cl.[5] .......................... A61F 5/00; A61G 7/05

[52] U.S. Cl. .......................................... 128/74; 128/70; 5/3; 5/67

[58] Field of Search ...................... 128/74, 73; 5/3, 6, 5/60, 66, 67, 68; 269/320, 325

[56] References Cited

U.S. PATENT DOCUMENTS

| | | | |
|---|---|---|---|
| 1,286,184 | 11/1918 | McManis . | |
| 1,319,227 | 10/1919 | Koenigkramer . | |
| 1,329,611 | 2/1920 | Koenigkramer . | |
| 1,351,482 | 8/1920 | McManis . | |
| 1,371,502 | 3/1921 | McManis . | |
| 1,390,301 | 9/1921 | McManis et al. . | |
| 1,417,675 | 5/1922 | McManis . | |
| 1,453,013 | 4/1923 | Koenigkramer . | |
| 1,686,979 | 10/1928 | McManis . | |
| 1,938,006 | 12/1933 | Blanchard . | |
| 3,020,908 | 2/1962 | Daniels et al. | 128/77 X |
| 4,094,024 | 6/1978 | Benoit et al. | 5/68 X |
| 4,227,269 | 10/1980 | Johnston | 5/68 X |
| 4,271,545 | 6/1981 | Christian, III | 5/66 |
| 4,327,453 | 5/1982 | Sefton | 5/81 |
| 4,472,845 | 9/1984 | Chivetta et al. | 5/66 X |
| 4,546,967 | 10/1985 | Kecala | 128/74 X |
| 4,569,339 | 2/1986 | Barnes . | |
| 4,649,905 | 3/1987 | Barnes | 128/74 |
| 4,747,170 | 5/1988 | Knouse | 5/81 X |
| 4,856,128 | 8/1989 | Alsip et al. | 5/66 X |

*Primary Examiner*—Richard J. Apley
*Assistant Examiner*—Linda C. M. Dvorak
*Attorney, Agent, or Firm*—Mark G. Kachigian

[57] ABSTRACT

A patient table apparatus having a pad for supporting a patient with at least two sections, a lower body section which will tilt with respect to an upper body section about an axis transverse to the pad. The apparatus includes a spring mechanism to impart an upward force on the lower body section against the force of gravity on the patient. A motor extends or retracts the spring mechanism and controls for the motor are provided whereby the amount of upward force on the lower body section may be increased or decreased.

1 Claim, 4 Drawing Sheets

PATIENT TABLE APPARATUS

BACKGROUND OF THE INVENTION

1. Field of the Invention

The present invention relates to an articulated patient table apparatus which will facilitate manipulation of the patient for various treatments. In particular, the present invention relates to a patient table apparatus wherein a force to support the patient may be easily and quickly adjusted and wherein the table may be easily and quickly locked in or unlocked from a selected position.

2. Prior Art

Patient tables wherein the patient's body is manipulated during treatment are well known. One such treatment is known as flexion disc traction treatment. This treatment is often performed on a table having at least two sections; a lower body section that will tilt with respect to the upper body section about an axis transverse to the upper body section.

To perform the treatment, the patient mounts the table and lays face down on the table while the lower body section is locked in place. The lower body section is next unlocked. This requires the doctor to reach under the table and release the lock. Depending on the weight of the patient and the existing setting of the supporting force on the lower body section, the lower body section may tilt downward toward the floor. This can be unsettling, at best, and can even be painful to a patient with an injured back. The doctor or medical personnel treating the patient will then reach beneath the lower body section and increase the amount of upward force in order to offset the weight of the patient until the lower body section is at the same level as the upper body section. The doctor or other medical personnel will them alternately lower and then raise the lower body section while manipulating the back of the patient. Finally, before the patient departs from the table, the lower body section is again locked in place.

This procedure requires the doctor or medical personnel to reach under the table on numerous occasions and divert attention away from the patient.

The Applicant is aware of the following prior art patents:

| U.S. PAT. NO. | PATENTEE | ISSUE DATE |
|---|---|---|
| 1,286,184 | McManis | November 26, 1918 |
| 1,453,013 | Koenigkramer | April 24, 1923 |
| 1,319,227 | Koenigkramer | October 21, 1919 |
| 1,329,611 | Koenigkramer | February 3, 1920 |
| 1,351,482 | McManis | August 31, 1920 |
| 1,390,301 | McManis/Koenigkramer | September 13, 1921 |
| 1,371,502 | McManis | March 15, 1921 |
| 1,417,675 | McManis | May 30, 1922 |
| 1,686,979 | McManis | October 9, 1928 |
| 1,938,006 | Blanchard | December 5, 1933 |
| 4,569,339 | Barnes | February 11, 1986 |

Several of the early McManis patents (U.S. Pat. Nos. 1,286,184, 1,371,502, 1,417,675, and 1,686,979) as well as the Koenigkramer patents (U.S. Pat. Nos. 1,453,013, 1,319,227) provide for a section of a patient table to be resiliently supported or suspended by a spring or springs which are extendable or retractable by a slidable carriage or attachment which moves along parallel arms. Either a turning wheel or a crank rotates a rod or screw shaft which moves a block linearly. The table section may be locked in place by tightening a nut on a threaded bolt in order to clamp the lock bar to the parallel arms.

The McManis and Koenigkramer patent (U.S. Pat. No. 1,390,301) discloses a similar arrangement.

Koenigkramer (U.S. Pat. No. 1,329,611) provides for suspension of multiple sections of a patient table.

Blanchard (U.S. Pat. No. 1,938,006) discloses an adjustable coil spring wherein its resistance may be varied in response to downward pressure imposed on the patient pad through the body of the patient.

Barnes (U.S. Pat. No. 4,569,339) depicts a more recent patient table although little has changed from the aforementioned early patents in the suspension and locking mechanism.

Accordingly, it is a principal object and purpose of the present invention to provide a variable suspension mechanism for a patient table that may be adjusted by the doctor or medical personnel without having to turn or crank the mechanism beneath the table.

It is a further object and purpose of the present invention to provide a locking mechanism that may be operated to lock or unlock the table in a selected position by means of a foot lever.

SUMMARY OF THE INVENTION

A patient table apparatus of the present invention is articulated into two sections—an upper body section and a lower body section that may be tilted about an axis transverse to the pad.

A base, capable of resting on a floor, supports a pedestal which, in turn, supports a frame. Extending from the frame is an upright which that terminates in a knuckle. The lower body section includes a supporting boom which is pivotally connected to the frame at a shaft which runs transverse to the pad. With the shaft as the center point, the lower body section is allowed to move angularly about the center point.

Extending from the upright at the knuckle is a moment arm which is pivotally attached thereto The moment arm is spaced from the lower body section and runs substantially longitudinally along the lower body section.

A pair of extension springs resiliently supports the lower body section of the pad in response to the weight of the patient. One end of each spring is received in an eyelet in the frame. The opposite end of each spring is received in a spring connect having an eyelet. The spring connects are joined together by a slide bar adapted to slide along the underside of the moment arm.

The springs provide an upward force on the moment arm which imparts an upward force on a beam that extends between the moment arm and the supporting boom of the lower body section.

A motor has two drive directions and a shaft which rotates a threaded rod extending from the motor. The threaded rod lies within a channel provided in the moment arm.

A threaded nut bracket is received on the threaded rod. Rotation of the rod moves the bracket linearly. The nut bracket is secured to the slide bar so that rotation of the threaded rod results in movement of the spring connects.

A lock bar is pivotally attached at one end to the supporting boom of the lower body section. The opposite end of the lock bar extends through an opening in a lock bracket secured to the moment arm. The lock bar has a plurality of openings near the opposite end adapted to receive a pin mounted in the lock bracket.

The pin is urged toward the openings by a coil compression spring surrounding the pin.

A bottom foot lever is directly attached to the pin and acts to pry the pin out of engagement with the lock bar.

When the pin is disengaged from the lock bar by stepping on the bottom pedal, a top foot pedal may be depressed and wedged between the bottom pedal and lock bracket.

DETAILED DESCRIPTION OF THE PREFERRED EMBODIMENTS

Figure 1:
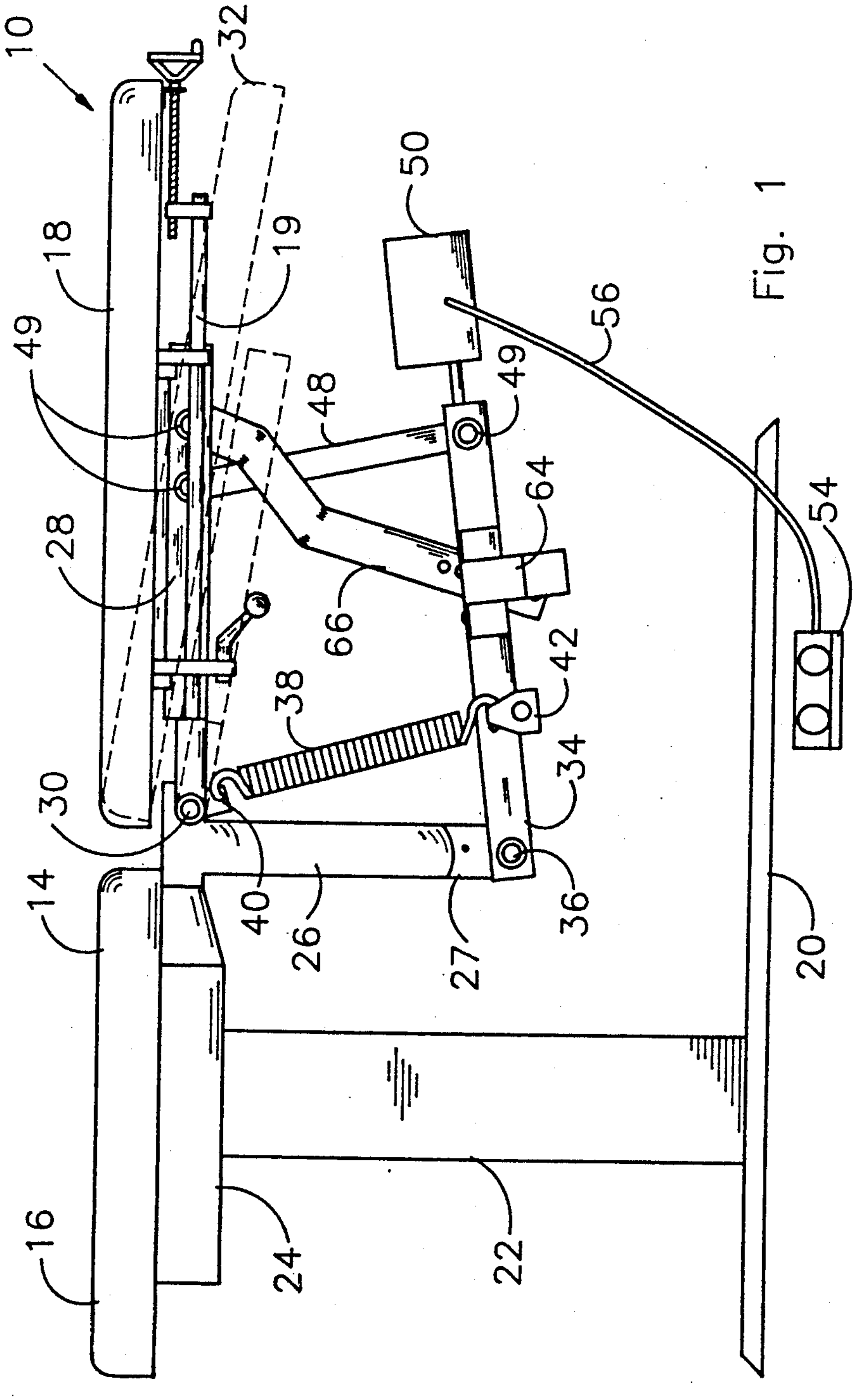
FIG. 1 is a side view of the patient table apparatus constructed in accordance with the present invention.

Referring to the drawings in detail, FIG. 1 depicts a patient table apparatus 10 embodying the present invention.

A patient (not shown) would lie on a table top or pad 14. The pad 14 is segmented into two sections—an upper body section 16 for the upper body of the patient and a lower body section 18 that, as will be described in detail, may be tilted about an axis transverse to the pad 14. While the present invention has two sections comprising the patient pad, it should be understood that additional sections might also be utilized to allow for different movements and different treatments.

The table may also incorporate other actions, such as lateral movement or rotation about a longitudinal axis. In the embodiment shown, longitudinal shaft 19 allows the lower body section to rotate.

A base 20 would rest on a floor (not shown). The base supports a pedestal 22 which, in turn, supports a frame 24. Extending from and rigidly secured to the frame is an upright 26. The upright terminates in a knuckle 27.

The lower body section includes a supporting boom 28. The boom 28 is pivotally connected to the frame 24 at shaft 30, which runs transverse to the pad 14.

The lower body section 18 is, thus, allowed to tilt or flex with respect to the upper body section 16. With the shaft 30 as the center point, the lower body section is allowed to move angularly about the center point. The highest position of the lower body section is seen in FIG. 1. The lower body section moves between the position shown in FIG. 1 and the position indicated by the dotted lines 32.

In the position shown in FIG. 1, the lower body section 18 is in the same plane as the upper body section. Consequently, a patient on the pad 14 will lie flat. When the lower body section is in the position shown by dotted lines 32, the patient's spine will be stretched.

Extending from the upright 26 at the knuckle 27 is a moment arm 34 which is pivotally attached thereto through use of a bolt 36 which passes through the knuckle 27. The moment arm is spaced from the lower body section and runs substantially longitudinally along the lower body section.

A pair of extension springs 38 (only one visible in FIG. 1) resiliently supports the lower body section of the pad in response to the weight of the patient. One end of each spring 38 is received in an eyelet 40 in the frame 24. The opposite end of each spring is received in a spring connect 42 having an eyelet 44. The spring connects 42 are joined together by a slide bar 46 which is adapted to slide along the underside of the moment arm 34.

Figure 2:
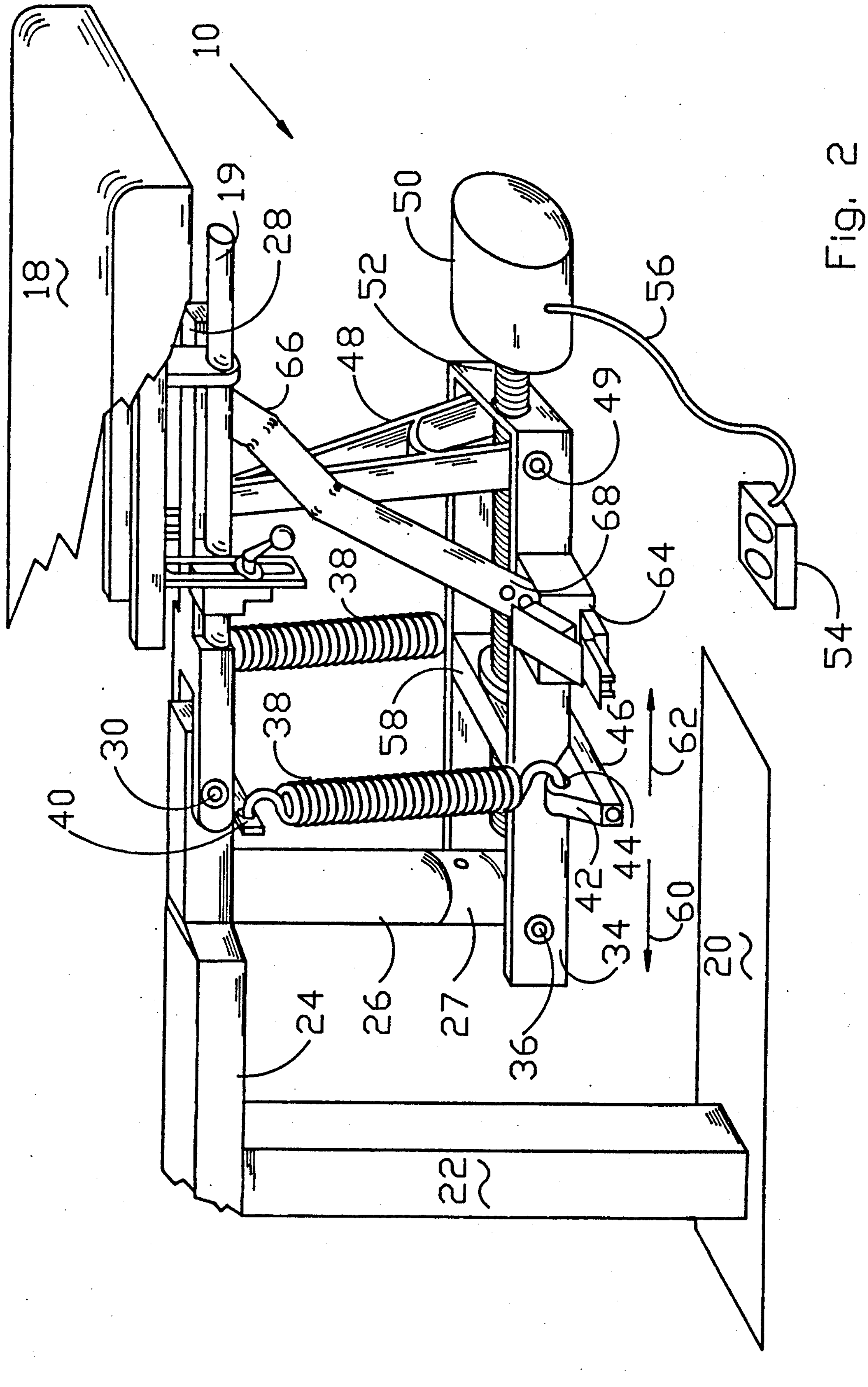
FIG. 2 is a perspective, cut-away view of the patient table apparatus shown in FIG. 1.

The arrangement of the springs 38 can best be seen in the cutaway perspective view shown in FIG. 2.

The springs 38 provide an upward force on the moment arm 34 which is pivotally attached to the upright 26. The force on the moment arm 34 imparts an upward force on a beam 48 that extends between the moment arm and the supporting boom 28 of the lower body section 18. The beam 48 is pivotally attached to both the moment arm and the supporting boom 28 by bolts 49.

A system is provided to vary the amount of upward force provided by the extension springs. An electric motor 50 is connected to and powered by household electric current (not shown). The motor has two drive directions and a shaft which rotates a threaded rod 52 extending from the motor shaft. The threaded rod 52 lies within a channel provided in the moment arm. The operation of the motor is controlled by a portable foot pedal 54 having two foot operated buttons. The foot switch is connected to the motor 50 by a cable 56. The foot switch may be moved to a location on the floor convenient to the doctor.

It will be observed that the beam 48 is not perpendicular to either the moment arm 34 or the supporting boom 28 but is juxtaposed at an angle between them. It has been found that an angle of approximately 25% from perpendicular is advantageous, although other angles may be used. When the lower body section 18 is depressed, the supporting boom 28 will move closer to the moment arm as the springs contract. The springs 38, thus, provide an upward force to the lower body section in opposition to the force of gravity on the patient prone on the lower body section.

A threaded nut bracket 58 is received on the threaded rod 52. Rotation of the threaded rod 52 will move the bracket linearly. The nut bracket 58 is secured to the slide bar 46 so that rotation of the threaded rod 52 results in movement of the spring connects 42.

The arrows 60 and 62 show the alternate directions of movement of the slide bar. In the direction shown in arrow 62, the springs 38 are extended, increasing the amount of upward force. In the direction shown in arrow 60, the springs are retracted, decreasing the amount of upward force. Additionally, as the springs are moved, the distance between the slide bar 46 and the pivot bolt 36 is changed, thus, changing the length of the moment arm, thereby varying the torque.

A locking mechanism 64 is provided to lock the lower body section 18 in a selected position. A lock bar 66 is pivotally attached at one end to the supporting boom 28 of the lower body section 18. The opposite end 68 of the lock bar 66 extends through an opening in a lock bracket 70 secured to the moment arm 34. As can be seen, the lock bar 66 is not perpendicular to either the moment arm 34 or the supporting boom. It has been found that an angle of approximately 25% from perpendicular is advantageous, although other angles may be used.

Figure 3:
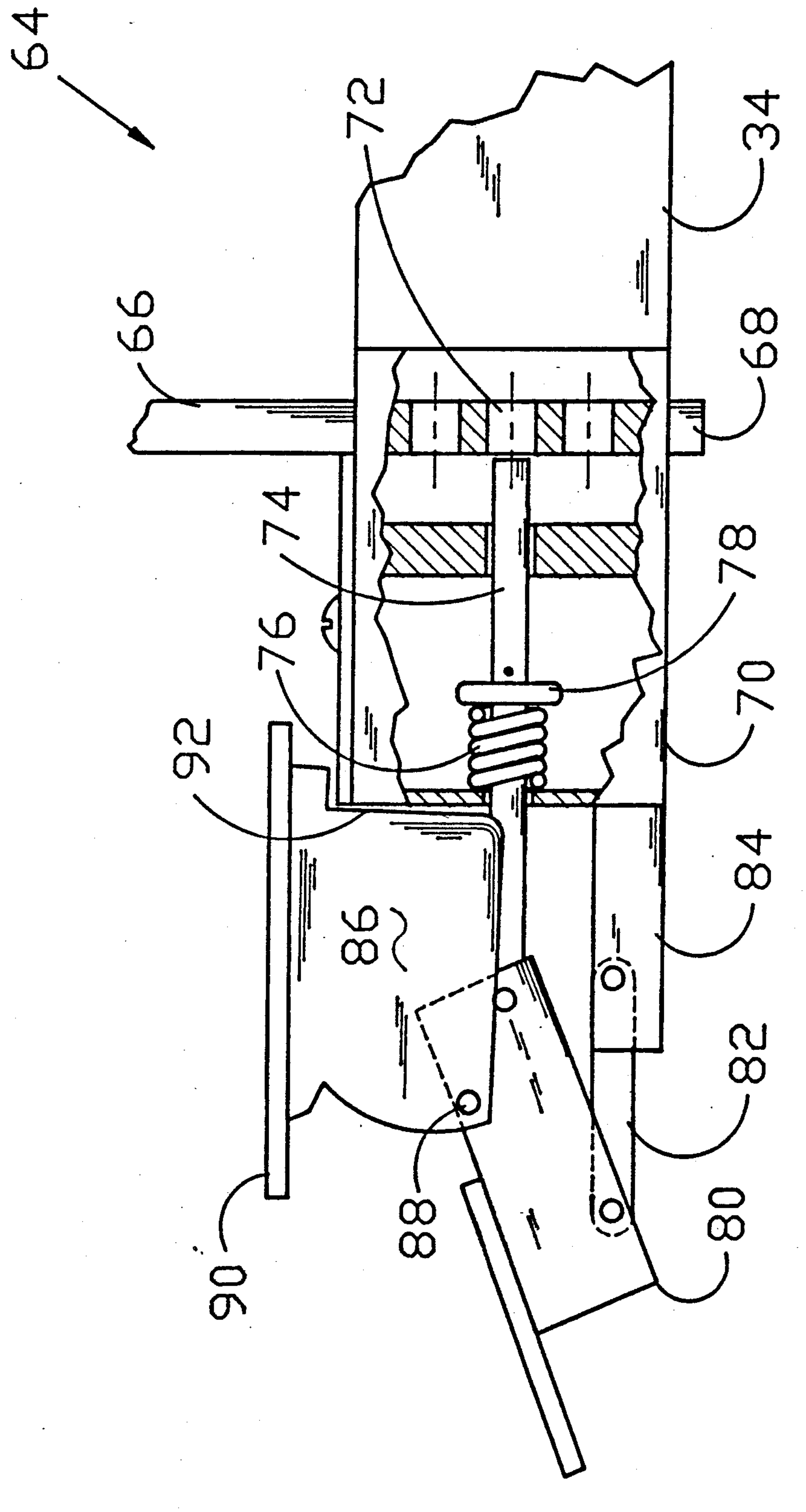
FIG. 3 is a cut-away view of the lock mechanism of the patient table apparatus shown in FIG. 1.
Figure 4:
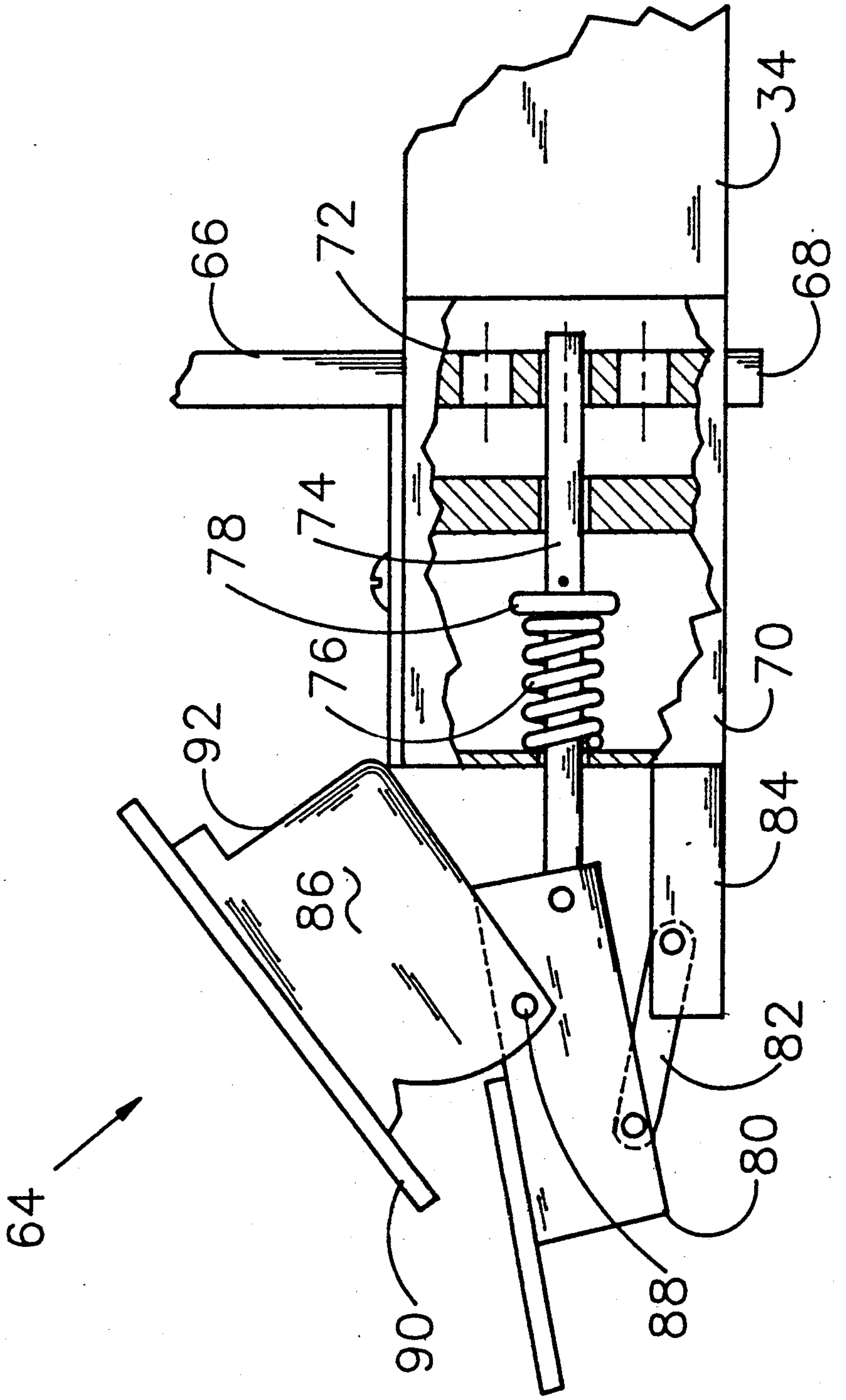
FIG. 4 is a cut-away view of the lock mechanism shown in FIG. 3 in the unlocked position.

FIG. 3 illustrates the unlocked position while FIG. 4 illustrates the locked position. When in the unlocked position, the end 68 is free to slide within the lock bracket 70 and the supporting boom 28 is free to move in response to the force of gravity on the patient and the opposing force of the springs 38.

The lock bar 66 has a plurality of openings 72 near the end 68 which are adapted to receive a pin 74 mounted in the lock bracket The pin 74 is urged toward the openings by a coil compression spring 76 that surrounds the pin. The spring is held in place on one side by the lock bracket 70 and on the other side by a stop washer 78.

The locking mechanism 64 may be easily operated by one foot while treating the patient. A bottom foot lever 80 is directly attached to the pin 74 and acts to pry the pin out of engagement with the lock bar.

Downward pressure of the bottom pedal 80 causes the pin to retract from the lock bar and the spring 76 to compress. Lateral movement of the bottom pedal 80 is prevented by a link 82 extending between the pedal 80 and an ear 84 on the lock bracket 70.

When the pin 74 is disengaged from the lock bar 66 by stepping on the bottom pedal 80, a top foot pedal 86 may be depressed and wedged between the bottom pedal 80 and the lock bracket 70. As seen in FIG. 3, the pin 74 will be retained away from the lock bar 66.

The bottom pedal 80 acts as a lever about pivot 88 received in the top foot pedal 86. To unlock the mechanism, the end 90 of the top foot pedal 86 and the bottom pedal 80 are depressed. Once the forward side 92 of the top foot pedal 86 is unwedged from the lock bracket 70, the foot pedals are released and the spring will urge the pin towards the lock bar 66.

In order to treat a patient, the lower body section is locked into the position shown in FIGS. 1 and 2 The bottom and top pedals 80 and 86 are depressed and then released in order to engage pin 74 with lock bar 66. The foot switch 65 will then be activated to activate the motor in order to move slide bar 46 in the direction of arrow 62, shown in FIG. 2. Once this is done, the upward force is at its greatest.

After the patient has mounted the table, the lock is released. The lower body section will remain in place because the upward force is greater than the force of gravity on the patient. The foot switch is again depressed to decrease the upward force to just offset the force of gravity on the patient. The lower body section will then respond to the light touch of the doctor. The lower body section can be flexed during treatment of the patient. When the treatment is completed, the table will again be locked in place before the patient dismounts.

As can be appreciated from the foregoing, all of the adjustments to the spring mechanism and the lock mechanism can be made without reaching under the table or diverting attention from the patient.

Whereas the present invention has been described in relation to the drawings attached hereto, it should be understood that other and further modifications, apart from those shown or suggested herein, may be made within the spirit and scope of this invention.

What is claimed is:

1. A patient table apparatus having a pad for supporting a patient with at least two sections, a lower body section which will tilt with respect to an upper body section about an axis transverse to said pad, which apparatus comprises:

a. adjustable spring means to impart an upward force on said lower body section against the force of gravity on the patient;

b. motor means to extend or retract said spring means;

c. control means to control said motor means whereby the amount of said upward force on said lower body section may be increased or decreased; and d. means to lock said lower body section in place in a selected position with respect to said upper body section, said means including a lock bar pivotally attached at one end to said upper body section, a spring loaded pin adapted to engage with at least one opening near the opposite end of said lock bar, foot-operated pedal means to retract said pin from said lock bar, and a foot depressible wedge to retain said pin in retracted position from said lock bar.

* * * * *